United States Patent [19]

Drabek et al.

[11] 4,219,564

[45] Aug. 26, 1980

[54] VINYLCYCLOPROPANECARBOXYLIC ACID-3-PHENOXY-α-VINYLBENZYL ESTERS, PROCESSES FOR PRODUCING THEM, AND THEIR USE IN COMBATING PESTS

[75] Inventors: Jozef Drabek, Oberwil; Peter Ackermann, Reinach; Saleem Farooq, Ettingen; Laurenz Gsell, Basel; Odd Kristiansen, Möhlin, all of Switzerland

[73] Assignee: Ciba-Geigy Corporation, Ardsley, N.Y.

[21] Appl. No.: 51,080

[22] Filed: Jun. 22, 1979

Related U.S. Application Data

[63] Continuation-in-part of Ser. No. 958,453, Nov. 6, 1978, abandoned.

[51] Int. Cl.$^2$ .................... C07C 69/74; A01N 9/30
[52] U.S. Cl. ................................ 424/305; 560/124
[58] Field of Search ........................ 560/124; 424/305

[56] References Cited

U.S. PATENT DOCUMENTS

| | | | |
|---|---|---|---|
| 3,927,068 | 12/1975 | Searle | 560/124 |
| 3,979,424 | 9/1976 | Searle | 560/124 |
| 3,981,903 | 9/1976 | Hirano | 560/124 |
| 4,024,163 | 5/1977 | Elliott | 560/124 |
| 4,100,297 | 7/1978 | Grandadem | 424/304 |
| 4,152,455 | 5/1979 | Engel | 560/124 |

FOREIGN PATENT DOCUMENTS 2706222  8/1977  Fed. Rep. of Germany.

*Primary Examiner*—Norman Morgenstern
*Assistant Examiner*—Michael Shippen
*Attorney, Agent, or Firm*—Harry Falber

[57] ABSTRACT

Vinylcyclopropanecarboxylic acid-3-phenoxy-α-vinylbenzyl esters of the formula $$\begin{array}{c} X_1 \\ \phantom{X}\diagdown \\ X_1 \phantom{\diagdown} \end{array} C=CH-CH \begin{array}{c} \phantom{X} \\ \diagdown \\ \diagup C \diagdown \\ CH_3 \phantom{\diagdown} Y \end{array} CH-COO-CH \begin{array}{c} \phantom{X} \\ \diagdown \\ C-X_2 \\ \| \\ CH-X_2 \end{array} -\!\!\!\bigcirc\!\!-O-\!\!\!\bigcirc$$

in which
 $X_1$ is fluorine, chlorine or bromine,
 $X_2$ is hydrogen or bromine, and
 Y is hydrogen or methyl, processes for producing them, and their use in combating pests.

7 Claims, No Drawings

VINYLCYCLOPROPANECARBOXYLIC ACID-3-PHENOXY-α-VINYLBENZYL ESTERS, PROCESSES FOR PRODUCING THEM, AND THEIR USE IN COMBATING PESTS

RELATED APPLICATION

This application is a continuation-in-part of application Ser. No. 958,453, filed Nov. 6, 1978, now abandoned.

The present invention relates to vinylcyclopropanecarboxylic acid-3-phenoxy-α-vinylbenzyl esters, to processes for producing them, and to their use in combating pests.

The vinylcyclopropanecarboxylic acid-3-phenoxy-α-vinylbenzyl esters have the formula

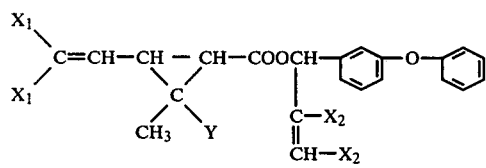

in which
X$_1$ is fluorine, chlorine or bromine,
X$_2$ is hydrogen or bromine, and
Y is hydrogen or methyl.

The compounds of the formula I are produced by methods known per se, for example as follows:

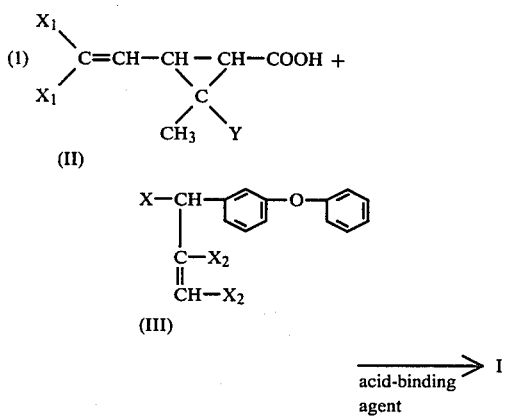

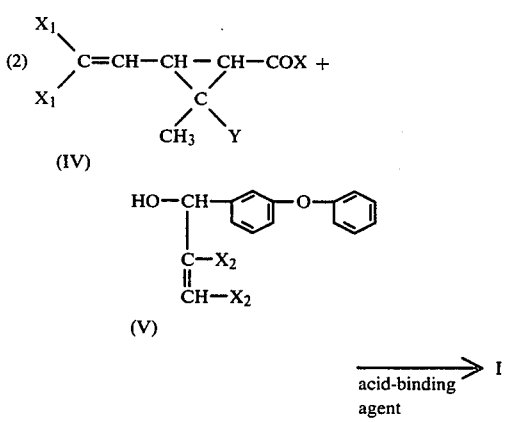

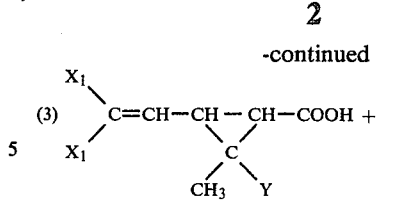

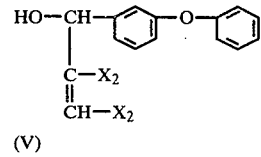

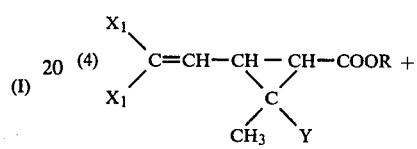

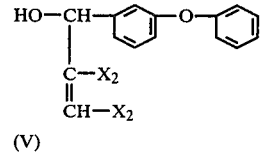

In the formulae II to VI, the symbols X$_1$, X$_2$ and Y have the meanings given under the formula I.

X in the formulae III and IV is a halogen atom, particularly chlorine or bromine; and R in the formula VI is C$_1$–C$_4$ alkyl, especially methyl or ethyl. Suitable acid-binding agents for the processes 1 and 2 are in particular tertiary amines, such as trialkylamine and pyridine, also hydroxides, oxides, carbonates and bicarbonates of alkali metals and alkaline-earth metals, and also alkali metal alcoholates, such as potassium-tertbutylate and sodium methylate. The water-binding agent used for the process 3 can be for example dicyclohexylcarbodiimide. The processes 1 to 4 are performed at a reaction temperature of between −10° and +120° C., usually between 20° and 80° C., under normal or elevated pressure, and preferably in an inert solvent or diluent. Suitable solvents or diluents are for example: ethers and ethereal compounds, such as diethyl ether, dipropyl ether, dioxane, dimethoxyethane and tetrahydrofuran; amides such as N,N-dialkylated carboxylic acid amides; aliphatic, aromatic as well as halogenated hydrocarbons, especially benzene, toluene, xylene, chloroform and chlorobenzene; nitriles such as acetonitrile; dimethylsulfoxide and ketones such as acetone and methyl ethyl ketone.

The starting materials of the formulae II, IV and VI are known and can be produced by methods analogous to known methods. Disclosures relating to such starting materials may, for example, be found in DOS No. 2,142,546. The preparation of starting materials III and V is described hereinafter.

Unless homogeneous optically active starting materials are used in the production process, the compounds of the formula I are obtained as mixtures of various optically active isomers. The different isomeric mixtures can be separated by known methods into the individual isomers. By 'compounds of the formula I' are meant both the individual isomers and mixtures thereof.

The compounds of the formula I are suitable for combating various animal and plant pests. They are suitable in particular for combating insects and phytopathogenic mites and ticks, for example of the orders Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera.

Compounds of the formula I are especially suitable for combating insects which damage plants, particularly insects which damage plants by eating, in crops of ornamental plants and useful plants, especially in cotton crops, (for example against *Spodoptera littoralis* and *Heliothis virescens*) and in crops of vegetables (for example against *Leptinotarsa decemlineata* and *Myzus persicae*). The active substances of the formula I also exhibit a very favourable action against flies, such as *Musca domestica*, and against mosquito larvae.

The acaricidal and insecticidal action can be substantially broadened and adapted to suit given circumstances by the addition of other insecticides and/or acaricides. Suitable additives are, for example, organic phosphorus compounds, nitrophenols and derivatives thereof, formamidines, ureas, other pyrethrin-like compounds, and also carbamates and chlorinated hydrocarbons.

Compounds of the formula I are combined particularly advantageously also with substances which have a synergistic or intensifying effect on pyrethroids. Examples of such compounds are, inter alia, piperonylbutoxide, propynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates, 1,2-methylenedioxy-4-(2-octylsulfonyl)-propyl)-benzene and N-(2-ethylhexyl)-bicyclo-(2,2,1)-heptene(2)-2,3-dicarboximide.

Compounds of the formula I can be used on their own or together with suitable carriers and/or additives. Suitable additives can be solid or liquid and they correspond to the substances common in formulation practice, such as natural or regenerated substances, solvents, dispersing agents, wetting agents, adhesives, thickeners, binders and/or fertilisiers.

The compositions according to the invention are produced in a manner known per se by the intimate mixing and/or grinding of the active substances of the formula I with suitable carriers, optionally with the addition of dispersing agents or solvents, which are inert to the active substances. The active substances can be obtained and used in the following forms:

Solid Preparations:
  dusts, scattering agents, granules (coated granules, impregnated granules and homogeneous granules);
Liquid Preparations
  (a) water-dispersible concentrates of active substance: wettable powders, pastes or emulsions;
  (b) solutions.

The content of active substance in the compositions described is between 0.1 and 95%, it is to be mentioned in this respect that with application from an aeroplane, or by other suitable devices, concentrations of up to 99.5% or even the pure active substance can be used.

The active substances of the formula I can be formulated for example as follows (parts are by weight).
Dusts The following substances are used to produce (a) a 5% dust, and (b) a 2% dust:

(a)

5 parts of active substance, and
95 parts of talcum; and (b)

2 parts of active substance,
1 part of highly dispersed silicic acid, and
97 parts of talcum.

The active substance is mixed and ground with the carriers.
Granulate
The following ingredients are used to produce a 5% granulate:
5 parts of active substance,
0.25 part of epichlorohydrin,
0.25 part of cetyl polyglycol ether,
3.50 parts of polyethylene glycol, and
91 parts of kaolin (particle size 0.3–0.8 mm).

The active substance is mixed with epichlorohydrin and dissolved in 6 parts of acetone, and the polyethylene glycol and cetyl polyglycol ether are then added. The solution obtained is sprayed onto kaolin and the acetone is subsequently evaporated off in vacuo.
Wettable powders
The following constituents are used to produce (a) a 40%, (b) and (c) a 25%, and (d) a 10% wettable powder:

(a)

40 parts of active substance,
5 parts of sodium lignin sulfonate,
1 part of sodium dibutyl-naphthalene sulfonate, and
54 parts of silicic acid;

(b)

25 parts of active substance,
4.5 parts of calcium lignin sulfonate,
1.9 parts of Champagne chalk/hydroxyethyl cellulose mixture (1:1),
1.5 parts of sodium dibutyl-naphthalene sulfonate,
19.5 parts of silicic acid,
19.5 parts of Champagne chalk, and
28.1 parts of kaolin;

(c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminum silicate,
16.5 parts of kieselguhr, and
46 parts of kaolin; and (d)

10 parts of active substance,
3 parts of a mixture of the sodium salts of saturated fatty alcohol sulfates,
5 parts of naphthalenesulfonic acid/formaldehyde condensate, and
82 parts of kaolin.

The active substance is intimately mixed in suitable mixers with the additives, and the mixture is then ground in the appropriate mills and rollers to obtain wettable powders which can be diluted with water to give suspensions of the desired concentration.

Emulsifiable concentrates

The following substances are used to produce (a) a 10%, (b) a 25% and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkylarylsulfonate calcium salt,
40 parts of dimethylformamide, and
43.2 parts of xylene;

(b)

25 parts of active substance,
2.5 parts of epoxidised vegetable oil,
10 parts of an alkylarylsulfonate/fatty alcohol polyglycol ether mixture,
5 parts of dimethylformamide, and
57.5 parts of xylene; and (c)

50 parts of active substance,
4.2 parts of tributylphenol-polyglycol ether,
5.8 parts of calcium-dodecylbenzenesulfonate,
20 parts of cyclohexanone, and
20 parts of xylene.

Emulsions of the concentration required can be prepared from these concentrates by dilution with water.

EXAMPLE 1

Manufacture of
3-phenoxy-α-(1′,2′-dibromovinyl)-benzylalcohol (a) With stirring and in a nitrogen atmosphere 150 ml tetrahydrofuran in which 12–14 g/h acetylene was introduced were added successively (in 3 hours) to a suspension of ethylmagnesia-bromide (produced with 30 g of ethylbromide and 6 g magnesia). The resulting solution of ethynylmagnesia-bromide was cooled to 0° C. and then added dropwise to a solution of 35.8 g 3-phenoxy-benzaldehyde in 25 ml tetrahydrofuran.

After 8 hours stirring at room temperature, the reaction solution was added dropwise to 750 ml of a saturated ammonia-chloride solution. After 30 minutes stirring the organic phase was separated, dried with sodium sulfate and chromatographed over silicagel with hexan and ether 4:1 as diluent. There was obtained 24 g of the compound of the formula

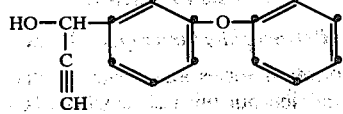

having a refractive index of $n_D^{32°} = 1.5798$.

(b) With stirring and under skylight lighting, 16 g bromine in 20 ml CCl$_4$ were added successively (in 2 hours) at a temperature of 10° to 20° C. to a solution of 22.4 g 3-phenoxy-α-(ethynyl)-benzyl-alcohol in 80 ml CCl$_4$.

After stirring for 10 hours at room temperature, the CCl$_4$ was distilled off.

There was obtained the compound of the formula

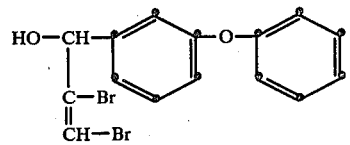

having a refractive index of $n_D^{35°} = 1.6210$.

Manufacture of 3-phenoxy-α-vinyl-benzylalcohol

With stirring, at room temperature and under normal pressure, hydrogen was introduced (3.37 l H$_2$; 0° C./760 mm Hg) in a solution of 33.7 3-phenoxy-α-ethynylbenzylalcohol in 340 ml dioxan and 1.7 g Lindlar catalysator.

After filtration and dilution with water the product was extracted with ether. After drying of the ether extracts with sodium sulfate and evaporation of the ether the product was chromatographed over silicagel with hexan and ether 1:1 as eluent.

There was obtained the compound of the formula

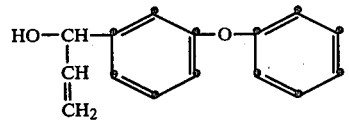

having a refractive index of $n_D^{32°} = 1.5832$.

Production of
2,2-dimethyl-3-(2,2-dichlorovinyl)-cyclopropanecarboxylic acid-3-(phenoxy)-α-vinylbenzyl ester 3.2 g of pyridine in 10 ml of benzene is added dropwise at 5° C. to a solution of 8 g of 3-phenoxy-α-vinylbenzyl alcohol in 30 ml of benzene, and at 10° C. is subsequently added 8 g of 2,2-dimethyl-3-(dichlorovinyl)-cyclopropanecarboxylic acid chloride. The reaction mixture is stirred for two hours at room temperature and is then allowed to stand for 12 hours. In further processing, the reaction mixture is diluted with ice water, the organic phase is extracted 3 times with 100 ml of 3% HCl solution each time and 3 times with 100 ml of 3% sodium bicarbonate solution each time; it is dried over sodium sulfate, and the benzene is distilled off. There is obtained the compound of the formula

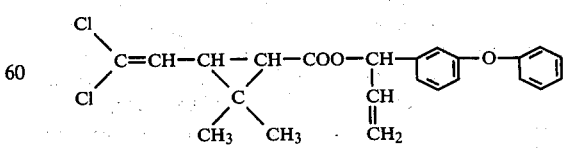

as colourless oil have a refractive index of $n_D^{40} = 1.5710$. (isomeric mixture 40% cis and 60% trans compound)

The following compounds are produced in an analogous manner:

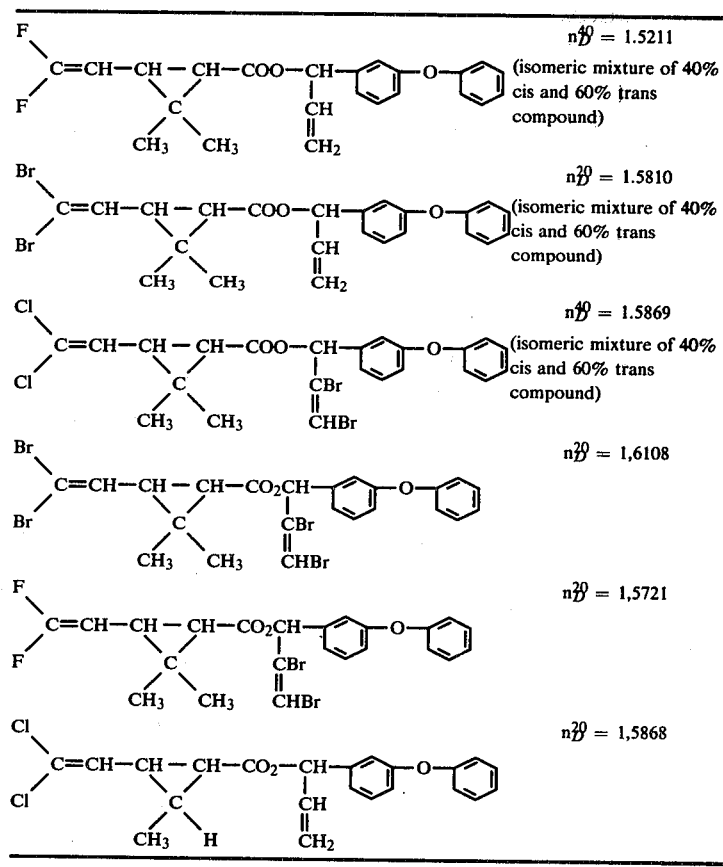

EXAMPLE 2

(A) Insecticidal stomach-poison action

Cotton plants were sprayed with a 0.05% aqueous emulsion of the active substance (obtained from a 10% emulsifiable concentrate).

After drying of the coating, larvae of *Spodoptera littoralis* in the L$_3$-stage and of *Heliothis virescens* in the L$_3$-stage were placed onto the cotton plants. The test was carried out at 24° C. with 60% relative humidity.

Compounds according to Example 1 exhibited in the above test a good insecticidal stomach-poison action against larvae of *Spodoptera littoralis* and *Heliothis virescens*.

EXAMPLE 3

Acaricidal action

*Phaseolus vulgaris* plants were infested, 12 hours before the test for acaricidal action, with an infested piece of leaf from a mass culture of *Tetranychus urticae*. The transferred mobile stages were sprayed with the emulsified test preparations from a chromatography-sprayer in a manner ensuring no overflow of the spray liquor. An assessment was made after 2 and 7 days, by examination under a binocular microscope, of the living and of the dead larvae, adults and eggs, and the results were expressed as percentages. The treated plants were kept during the "holding time" in greenhouse compartments at 25° C.

Compounds according to Example 1 exhibited in the above test a good action against adults, larvae and eggs of *Tetranychus urticae*.

EXAMPLE 4

Action against ticks (A) *Rhipicephalus bursa*

For each concentration, 5 adult ticks and 50 tick larvae, respectively, were counted into a small glass test tube, and immersed for 1 to 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

The evaluation in the case of the adults was made after 2 weeks and in the case of the larvae after 2 days. There were two repeats for each test.

(B) *Boophilus microplus* (larvae)

With a dilution series analogous to that of Test A, tests were carried out with 20 sensitive larvae and OP-resistant larvae, respectively (resistance is with respect to diazinon compatibility).

Compounds according to Example 1 were effective in these tests against adults and larvae of *Rhipicephalus bursa* and against sensitive and OP-resistant larvae, respectively, of *Boophilus microplus*.

We claim:

1. A compound of the formula

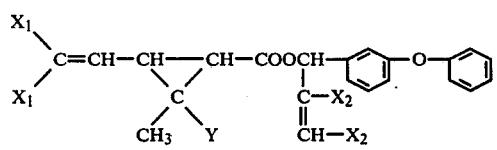

wherein

X₁ is fluorine, chlorine or bromine,

X₂ is hydrogen or bromine, and

Y is hydrogen or methyl.

2. The compound according to claim 1 of the formula

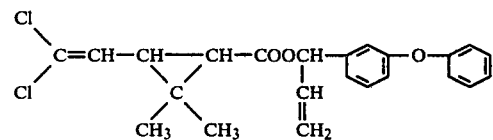

3. The compound according to claim 1 of the formula

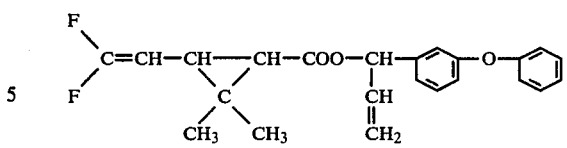

4. The compound according to claim 1 of the formula

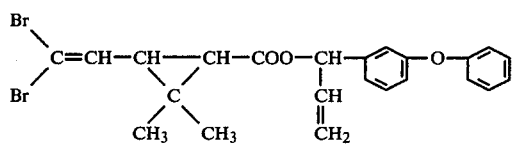

5. The compound according to claim 1 of the formula

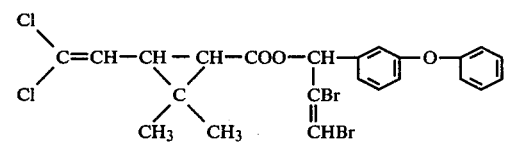

6. An insecticidal and acaricidal composition comprising an insecticidally and acaricidally effective amount of a compound according to claim 1, together with a suitable carrier therefor.

7. A method for combatting insects and acarids which comprises applying thereto of the locus thereof an insecticidally and acaricidally effective amount of a compound according to claim 1.

* * * * *

UNITED STATES PATENT AND TRADEMARK OFFICE
CERTIFICATE OF CORRECTION

PATENT NO. : 4,219,564
DATED : August 26, 1980
INVENTOR(S) : Jozef Drabek, Peter Ackermann, Saleem Farooq, Laurenz Gsel, Odd Kristiansen It is certified that error appears in the above-identified patent and that said Letters Patent are hereby corrected as shown below:

Cover page, column 1 should be

--[30] Foreign Application Priority Data

Nov. 9, 1977 [CH] Switzerland.........13663/77
Sept. 28, 1978 [CH] Switzerland.......10139/78 --.

Signed and Sealed this

Thirteenth Day of January 1981

[SEAL]

Attest:

SIDNEY A. DIAMOND

Attesting Officer

Commissioner of Patents and Trademarks